(12) United States Patent
Vanmoor

(10) Patent No.: US 6,476,072 B1
(45) Date of Patent: Nov. 5, 2002

(54) METHOD OF TREATING MENSTRUAL PAIN BY ENHANCING THE EFFECTIVENESS OF THE HUMAN IMMUNE SYSTEM

(76) Inventor: Arthur Vanmoor, 22 SE. 4 St., Boca Raton, FL (US) 33432-6016

( * ) Notice: Subject to any disclaimer, the term of this patent is extended or adjusted under 35 U.S.C. 154(b) by 0 days.

(21) Appl. No.: 09/717,635

(22) Filed: Nov. 21, 2000

(51) Int. Cl.⁷ .............................................. A61K 31/198
(52) U.S. Cl. ...................................................... 514/562
(58) Field of Search .................................. 514/562, 563

(56) References Cited

U.S. PATENT DOCUMENTS 5,214,062 A * 5/1993 Mark et al. .................. 514/369
6,113,907 A * 9/2000 Khwaja et al. .......... 424/195.1
6,143,722 A * 11/2000 Melin et al. .................... 514/17

FOREIGN PATENT DOCUMENTS

WO             00/51623      *    9/2000

* cited by examiner

*Primary Examiner*—Phyllis G. Spivack

(57) ABSTRACT

A method of treating menstrual pain in a person in need of such treatment is disclosed, which comprises enhancing the effectiveness of the person's immune system by the administration to such person at least one aliphatic sulfur compound of the formula (I)

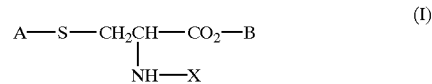

in which A is hydrogen or a carboxymethylene —$CH_2CO_2H$ group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

23 Claims, No Drawings

METHOD OF TREATING MENSTRUAL PAIN BY ENHANCING THE EFFECTIVENESS OF THE HUMAN IMMUNE SYSTEM

BACKGROUND OF THE INVENTION

1. Field of the Invention

This invention relates to a method of treating a female suffering from menstrual pain with an agent that enhances the effectiveness of the human immune system to mitigate and where possible eliminate the pain.

2. Description of Related Art

The human immune system functions to maintain human individuality by fighting off foreign entities. The MERCK MANUAL, 16th edition, published 1992, at pages 279 to 303, which portion is here incorporated by reference, contains a detailed description of the parts of the immune system and of immunodeficiency diseases and hypersensitivity disorders to which it is subject. A table at pages 284-5 titled "Cytokines" lists the major effects of such cytokines or immunoeffective polypeptides as interleukin types, interferon types, alpha- and beta-tumor necrosis factor, three types of colony-stimulating factor, and alpha- and beta-transforming growth factor. A table at page 303 lists disorders with increased susceptibility to unusual infections. Nothing in this publication relates to menstrual pain or remedies therefor.

As is well known, the human female has been afflicted with menstrual pain since antiquity, and remedies have been sought for generations by a great variety of methods. Current practice tends to rely on self-prescribed over-the-counter analgesics such as acetaminophen and ibuprofen while the search for more effective remedies continues. However, the search for better remedies for this as well as other suffering conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache, elevated blood pressure, facial pimples, signs of the so-called common cold, and pains in a joint by administering selected foods, food ingredients, and relatively harmless household chemicals as trigger substances, and to use these as research tools to study the effectiveness of certain nutrient substances in relieving these artificially produced conditions as well as their natural counterparts. As a result, certain water soluble amino carboxylic acid compounds are disclosed in U.S. Pat. No. as effective against facial pimples; certain water soluble amino carboxylic acid compounds are disclosed in U.S. Pat. No. 5,626,831 as effective against the common cold; certain water soluble amino carboxylic acid compounds are disclosed in U.S. Pat. No. 5,707,967 as effective against headache; certain water soluble amino carboxylic acid compounds are disclosed in U.S. Pat. No. 5,708,029 as effective against elevated blood pressure, and certain water soluble amino carboxylic acid compounds are disclosed in U.S. Pat. No. 5,767,157 as effective against pain in a joint.

SUMMARY OF THE INVENTION

In accordance with this invention, there is provided a method of treating menstrual pain in a female person in need of such treatment, which comprises the administration to such person of at least one aliphatic sulfur compound. The effectiveness of the aliphatic sulfur compound according to the invention is believed to accompany enhancement of the effectiveness of the person's immune system.

The aliphatic sulfur compound preferably includes a sulfur-methylene moiety such as

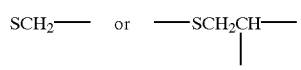

More preferably, the aliphatic sulfur compound also includes a carboxyl group, as in

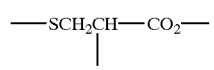

Still more preferably, the aliphatic sulfur compound is a sulfur-containing amino-acid derivative of an ethyl sulfide having the formula (I)

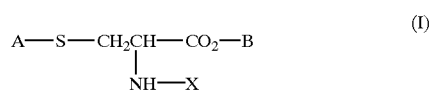

in which A is hydrogen or a carboxymethylene —$CH_2CO_2H$ group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

In this compound, the ethyl sulfide group

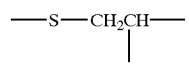

is believed to be responsible for the beneficial activity observed while the attached groups A, —NHX, and —$CO_2$B assist in delivering the compound to the site within the human organism where the beneficial activity is exerted.

In one preferred embodiment, A is hydrogen.

In a further preferred embodiment, A, B, and X are not simultaneously hydrogen.

Particularly suitable illustrative derivatives having the formula given above are tabulated by showing the assignments of A, B, and X in the above formula:

| Compound | A | B | X |
|---|---|---|---|
| 1 | —$CH_2CO_2H$ | H | H |
| 2 | H | H | $COCH_3$ |
| 3 | H | $CH_3$ | H.HCl |
| 4 | H | $C_2H_5$ | H.HCl |
| 5 | H | H | H |
| 6 | H | H | H.HCl |

The present invention is based on the recognition that enhancing the effectiveness of the immune system in a female person can be beneficial in augmenting the person's innate ability to resist the initiation of the process that leads to menstrual pain as well as to slow down, arrest, and even reverse that process. As a result, the occurrence and duration of menstrual pain is diminished or eliminated, and the quality of life is improved.

In increasing the effectiveness of the human immune system according to this invention, mega-nutrient doses of 2 to 20 grams of a compound or compounds of formula (I) can be administered from one to eight times daily, typically with meals and midway between meals, until reduction in the intensity of menstrual pain up to about 90% is obtained and the improvement in the user's condition permits reduction in dose level to a preventive maintenance dose and ultimately cessation of the treatment. Such doses can be administered in any convenient manner, as by oral administration in any of the usual dosage forms, such as tablets, capsules, solutions, and dispersions in liquid foods such as soups and fruit juices. Alternatively, there can be given sterile solutions by direct injection into the bloodstream of the person to be treated, as well as by rectal suppositories.

EXAMPLE 1

A group of female volunteers suffering menstrual pain was given ten gram portions of composition containing several compounds of formula (I) with each meal and at intervals of 2-3 hours between meals until the pain was diminished to no more than 10% of the original intensity. From then on the pain cleared without further intake of the composition.

What is claimed is:

1. A method of treating menstrual pain in a female person in need of such treatment, which comprises the oral administration to such person, of mega-nutrient doses of 2 to 20 grams up to eight times daily of at least one sulfur-containing amino-acid derivative having the formula (I)

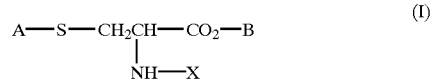

in which A is hydrogen or a carboxymethylene $-CH_2CO_2H$ group, B is hydrogen or an alkyl group having 1 to 3 carbon atoms, and X is hydrogen, or an acyl group $-CO-R$ in which R is an alkyl group having 1 to 3 carbon atoms, or a pharmaceutically acceptable salt of such compound, provided that A, B and X are not simultaneously hydrogen, and provided further that the total dose is at least 10 grams daily and not in excess of 160 grams daily.

2. The method of claim 1, wherein said amino-acid derivative is administered orally with food.

3. The method of claim 1, wherein said amino-acid derivative is administered by injection into the bloodstream.

4. The method of claim 1, wherein said amino-acid derivative is administered by rectal suppository.

5. The method of claim 1, wherein said amino-acid derivative is administered in one to eight daily doses of 2 to 20 grams each.

6. The method of claim 1, wherein the total of said amino-acid derivative administered daily is in the range of 10 to 80 grams.

7. The method of claim 1, wherein said amino-acid derivative is the compound of formula (I) in which A is $-CH_2CO_2H$, B is H, and X is H.

8. The method of claim 1, wherein said amino-acid derivative is the compound of formula (I) in which A is H B is H, and X is $COCH_3$.

9. The method of claim 1, wherein said amino-acid derivative is the compound of formula (I) in which A is H, B is $CH_3$, and X is H.HCl.

10. The method of claim 1, wherein said amino-acid derivative is the compound of formula (I) in which A is H, B is $C_2H_5$, and X is H.HCl.

11. The method of claim 1, wherein said person experiences relief from the effects of menstrual pain.

12. The method of claim 1 wherein after treatment menstrual pain is not detectable.

13. The method of claim 1, which comprises the administration of a plurality of sulfur-containing amino-acid derivatives having formula (I).

14. A method of treating menstrual pain in a female person in need of such treatment, which comprises enhancing the effectiveness of the person's immune system by the oral administration to such person of mega-nutrient doses of 2 to 20 grams up to eight times daily of at least one sulfur-containing amino-acid derivative having the formula (I)

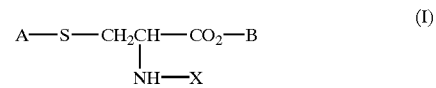

in which A is hydrogen or a carboxymethylene $-CH_2CO_2H$ group, B is hydrogen or an alkyl group having 1 to 3 carbon atoms, and X is hydrogen, or an aryl group $-CO-R$ in which R is an alkyl group having 1 to 3 carbon atoms, or a pharmaceutically acceptable salt of such compound, provided that A, B and X are not simultaneously hydrogen, and provided fiber that the total dose is at least 10 grams daily and not in excess of 160 grams daily.

15. The method of claim 14, which comprises the administration of a plurality of sulfur-containing amino-acid derivatives having formula (I).

16. The method of claim 14, wherein said amino-acid derivative is administered orally with food.

17. The method of claim 14, wherein said amino-acid derivative is administered by injection into the bloodstream.

18. The method of claim 14, wherein said amino-acid derivative is administered by rectal suppository.

19. The method of claim 14, wherein said amino-acid derivative is administered in one to eight daily doses of 2 to 20 grams each.

20. The method of claim 14, wherein the total of said amino-acid derivative administered daily is in the range of 10 to 80 grams.

21. The method of claim 14, wherein said amino-acid derivative is the compound of formula (I) in which A is $-CH_2CO_2H$, B is H, and X is H.

22. The method of claim 14, wherein said amino-acid derivative is the compound of formula (I) in which A is H, B is H, and X is $COCH_3$.

23. The method of claim 14, wherein said person experiences relief from the effects of menstrual pain.

* * * * *